(12) United States Patent
Poirier

(10) Patent No.: US 11,253,294 B1
(45) Date of Patent: Feb. 22, 2022

(54) IMPLANTABLE SPINE ROD CROSSLINK

(71) Applicant: Presidio Surgical, Inc., Alamo, CA (US)

(72) Inventor: David A. Poirier, Alamo, CA (US)

(73) Assignee: Presidio Surgical, Inc., Scottsdale, AZ (US)

( * ) Notice: Subject to any disclaimer, the term of this patent is extended or adjusted under 35 U.S.C. 154(b) by 431 days.

(21) Appl. No.: 15/631,469

(22) Filed: Jun. 23, 2017

(51) Int. Cl.
*A61B 17/70* (2006.01)

(52) U.S. Cl.
CPC ...... *A61B 17/7049* (2013.01); *A61B 17/7052* (2013.01); *A61B 17/7083* (2013.01)

(58) Field of Classification Search
CPC ............ A61B 17/7049; A61B 17/8004; A61B 17/8023
USPC .................................................. 606/280–299
See application file for complete search history.

(56) References Cited

U.S. PATENT DOCUMENTS

| | | | | | |
|---|---|---|---|---|---|
| 5,707,372 | A * | 1/1998 | Errico | ................ | A61B 17/7052 606/252 |
| 7,591,837 | B2 * | 9/2009 | Goldsmith | ........... | A61B 17/707 606/246 |
| 7,645,294 | B2 * | 1/2010 | Kalfas | ................ | A61B 17/7071 606/250 |
| 8,460,342 | B2 * | 6/2013 | Courtney | ........... | A61B 17/7052 606/252 |
| 8,920,471 | B2 * | 12/2014 | Barrus | ................ | A61B 17/7049 606/251 |
| 2014/0148856 | A1 * | 5/2014 | Ibarra | ................ | A61B 17/7052 606/276 |

* cited by examiner

*Primary Examiner* — Eduardo C Robert
*Assistant Examiner* — Tara Rose E Carter
(74) *Attorney, Agent, or Firm* — Heisler & Associates

(57) ABSTRACT

Spine rods are secured together by a crosslink which includes a central body with an arch therein curving around a gap, which allows a spinous process of an adjacent vertebrae, or other anatomical structure, to be located therein. The crosslink includes left and right extensions in a preferred embodiment which are movable relative to the body to accommodate both width adjustment for the crosslink and pivoting of distal ends of the crosslink relative to each other and relative to the body. After movement is accommodated, joints between the extensions in the body can be tightened to eliminate further movement. Clamps at distal ends of the crosslink secure the crosslink to adjacent spine rods. The arch has a bend angle above a horizontal plane to further facilitate avoiding interference with anatomical structures. The arch can be further bent if needed to a desired angle.

16 Claims, 4 Drawing Sheets

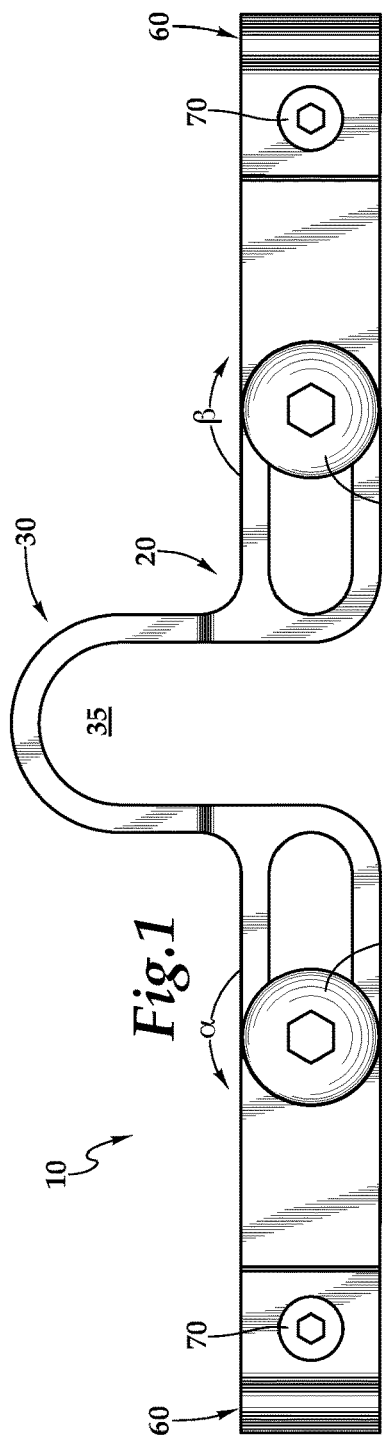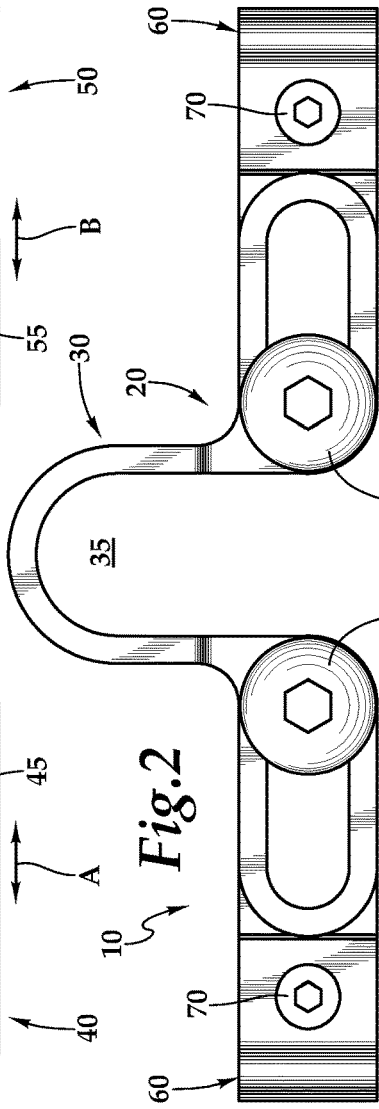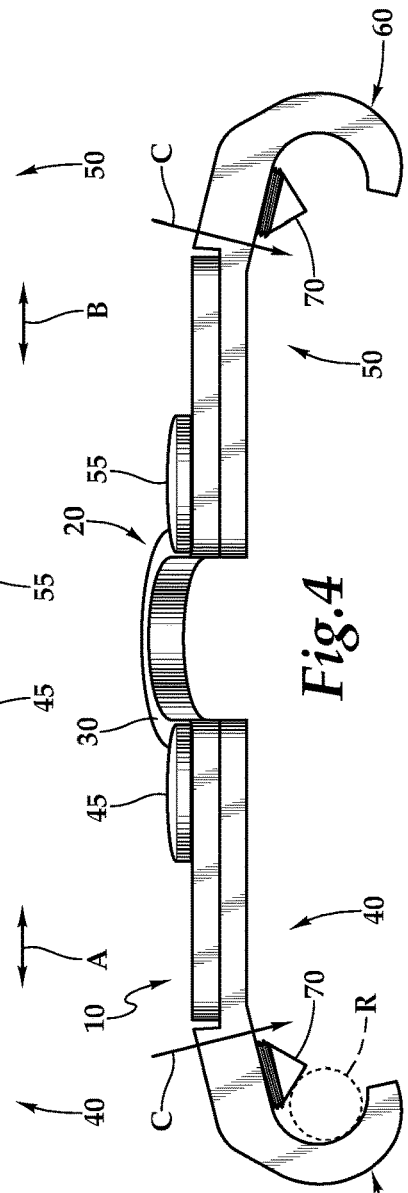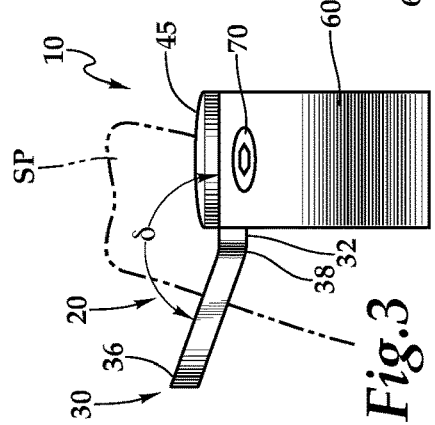

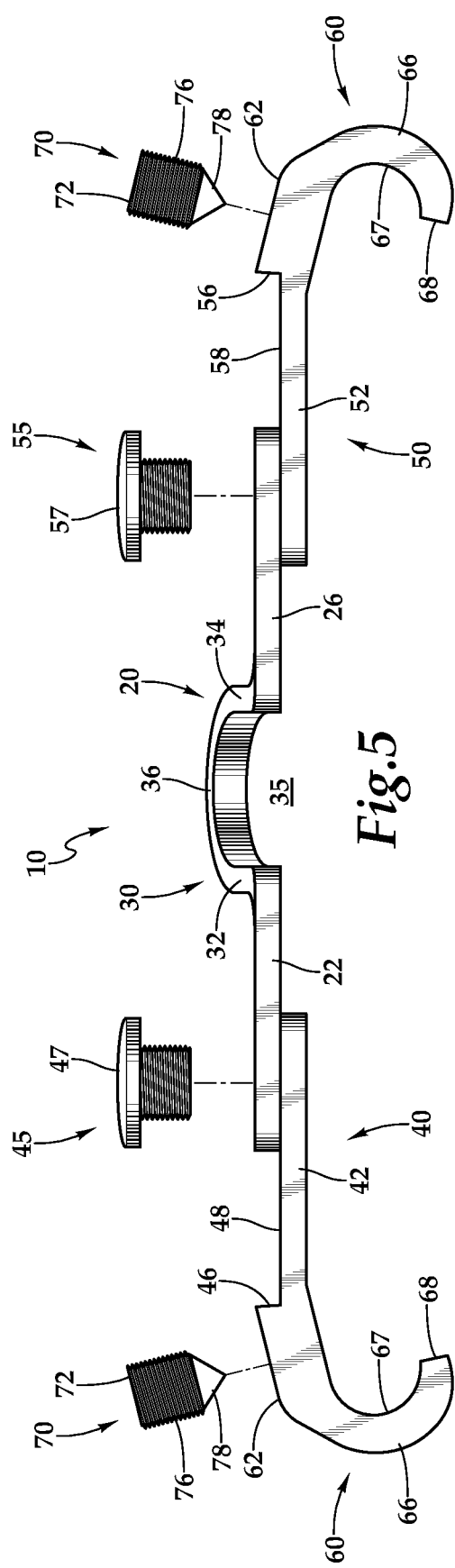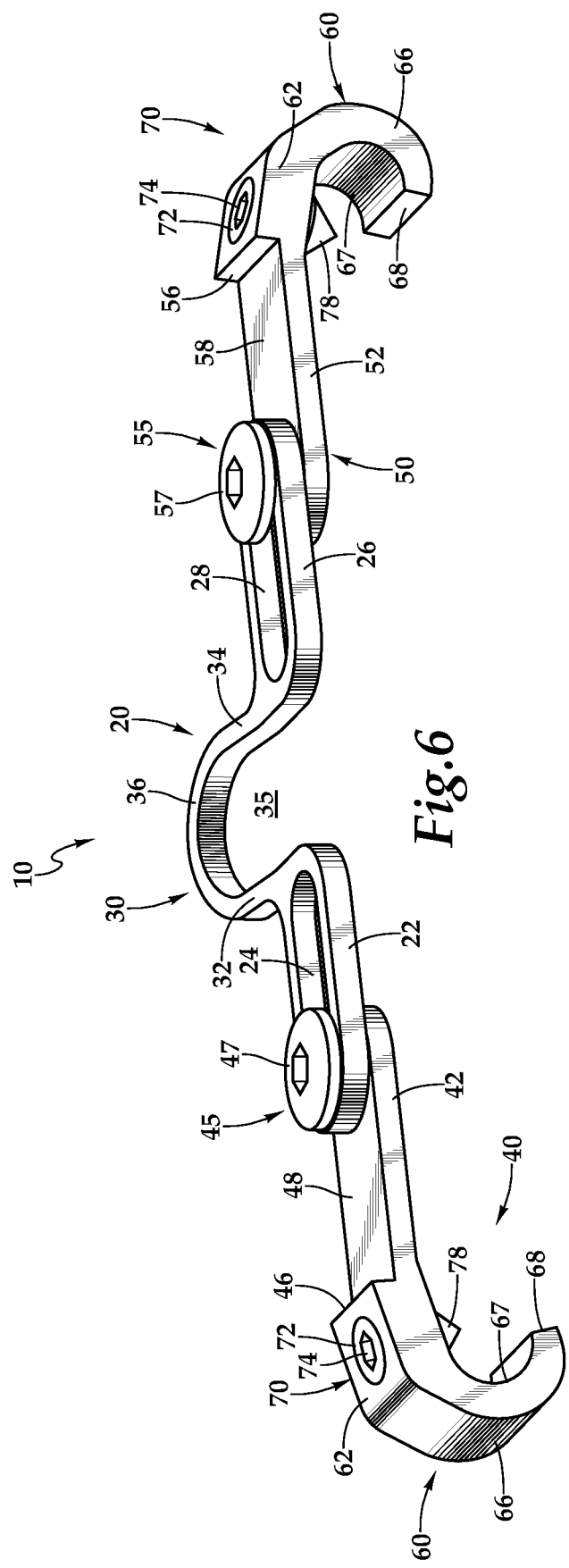

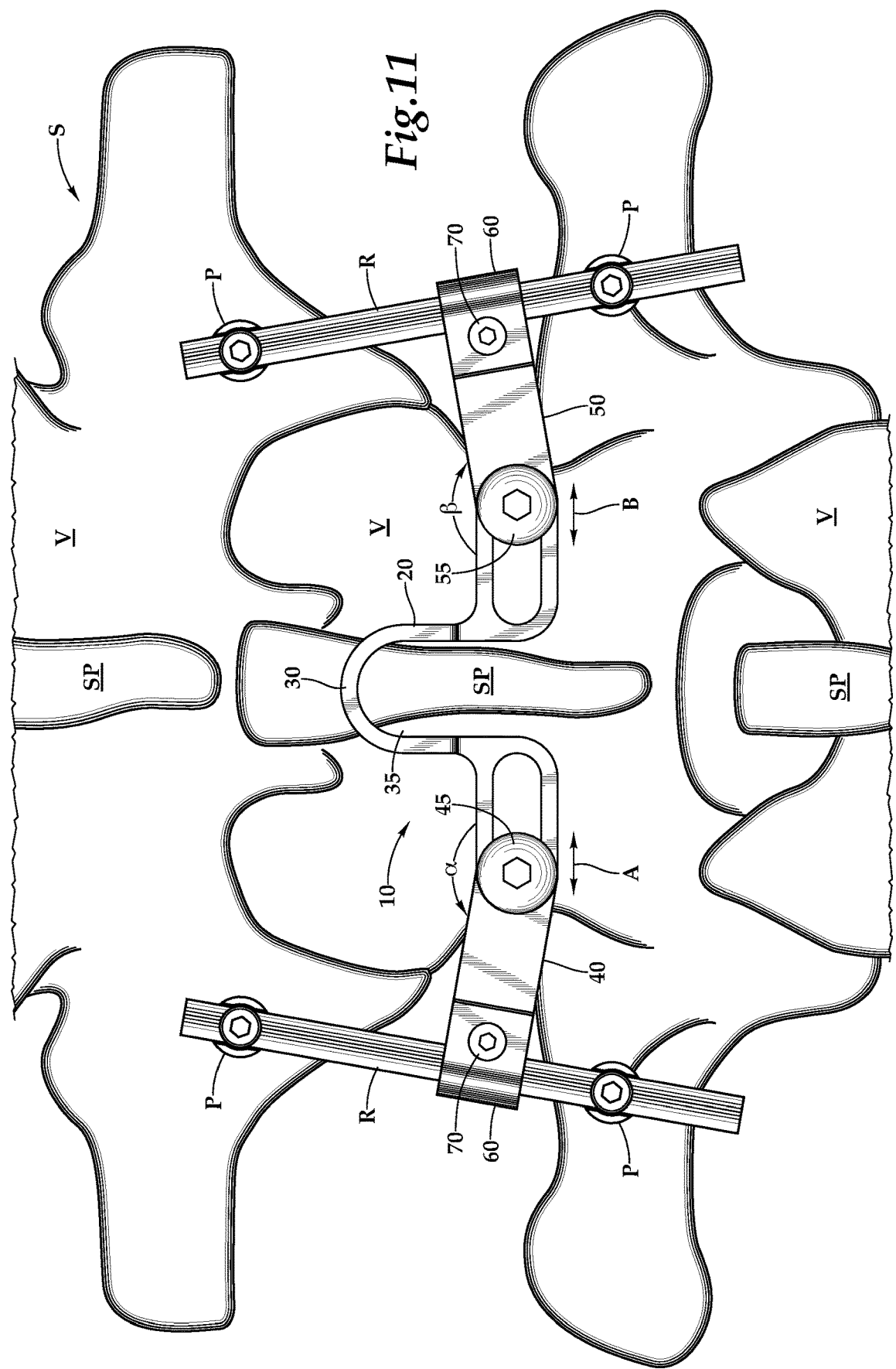

IMPLANTABLE SPINE ROD CROSSLINK

FIELD OF THE INVENTION

The following invention relates to crosslinks which are used to fasten between spine rods so they can stabilize each other at a surgical site within a patient. More particularly, this invention relates to crosslinks which are configured to avoid interference with anatomical structures and which can be easily adjusted in length and/or shape and easily tightened to spine rods.

BACKGROUND OF THE INVENTION

Often in spinal fusion procedures and other procedures where stabilization of the spine is indicated, spine rods are utilized. While spine rods can be used singly, quite often they are utilized in pairs, with each spine rod running generally parallel with the length of the spine and parallel with each other, but spaced laterally between left posterior and right posterior orientations relative to the spine. The spine rods are typically secured to the vertebrae of the spine through pedicle screws which are screwed into pedicles of various vertebrae to be held in position by the spine rod. Heads of the pedicle screws are configured so that they can clamp onto the spine rod and securely hold the spine to the spine rod. A spine rod can be as short as merely spanning a space between two adjacent vertebrae, with one pedicle screw near each end of the spine rod, or the spine rod can be longer and/or have more than two pedicle screws fastened to the spine rod.

In many instances it is desirable to secure the left and right spine rods together. It is known in the prior art to utilize a crosslink for such a purpose. Crosslinks generally are structures which extend laterally a distance similar to a space in-between the two spine rods. The crosslink is a rigid structure with some form of fastener at each end which allows the crosslink to be fastened to a spine rod at each end of the crosslink. Typically, some portion of each spine rod between pedicle screws is selected as a site for crosslink placement. When longer spine rods are implanted, more than one crosslink can be provided for securing the spine rods to each other.

One problem with prior art crosslinks is that an optimal position for crosslink placement (between pedicles and pedicle screws) often causes the crosslink to pass through an area where a "spinous process" of one of the vertebrae is located, the spinous process thus interfering with standard crosslink placement. Thus, sub-optimal solutions have been resorted to, including placing the crosslink at a less desirable location or removing at least a portion of the spinous process. Some crosslinks are known to include pivot joints at midpoints thereof. Such a pivot joint can accommodate spine rods which are not precisely parallel to each other and to some extent can allow for routing of the crosslink in a manner other than strictly linearly between ends at the crosslink. However, such pivoting crosslink designs do not have nearly enough adjustable positioning range to fully avoid the spinous process, especially for many of the spinal vertebrae, so that sub-optimal placement or spinous process removal is still required.

Furthermore, many crosslinks are not adjustable or only exhibit limited adjustability or present difficulty in utilizing adjustability features thereof. For many surgeons, use of a crosslink is seen as a non-critical item and placement of the crosslink needs to be balanced with other factors, such as minimizing the length of a surgical procedure, the degree to which the crosslink can be effectively tightened, and whether space is available for the crosslink. Thus a surgeon often decides not to utilize a crosslink at all. Accordingly, it is important to provide a crosslink which is easy to place, adjust and tighten; a crosslink having an optimal size and shape but which can still be rapidly placeable and securable to the spine rods at an optimal location. Such a crosslink also would preferably have a configuration which can completely avoid interference with the spinous process of adjacent vertebrae, so that the crosslink can be placed precisely where desired for optimal effectiveness and without requiring removal of any portion of the spinous process.

SUMMARY OF THE INVENTION

With this invention, a crosslink is provided which has a simple robust construction and facilitates size and shape adjustment, as well as having a clearance gap which is sized large enough to accommodate the spinous process of an adjacent vertebrae for a large portion of crosslink locations. The crosslink includes a body which has an arch therein at a central proportion thereof. The arch curves around a gap. The gap is sized large enough to allow the spinous process of a vertebrae to reside therein. The crosslink is preferably also adjustable both in length and shape, such as through joints which secure optional extensions to the central body. Ends of the crosslink include clamps or other spine rod fasteners which allow the crosslink to be secured to the left and right spine rods.

In a preferred embodiment disclosed, the body is configured to include a left wing and a right wing, which provide one portion of the joints. Separate extensions including a left extension and right extension are adjustably attachable to the left wing and the right wing respectively. The joint between the extensions and associated wings of the body includes a slot and a threaded hole. A bolt or other threaded fastener can pass through this slot and into the threaded hole, so that when the bolt is tightened, the extensions are fixed to the wings of the body. When these bolts are loosened, this joint accommodates length adjustment (up to the length of the slot) as well as pivoting to accommodate some degree of shape alteration for the crosslink.

In this preferred embodiment, the clamps or other spine rod fasteners are configured as a curve which includes a curving inner surface and a threaded stud which passes through a threaded hole in the extension at a strategic location which allows tightening of the threaded stud into the threaded hole to cause a space inboard of the curving inner surface to be reduced in size as the stud is tightened, and thus allowing the stud and curving inner surface to act together to clamp a spine rod therebetween.

Also in this preferred embodiment, the arch in the body preferably is angled slightly at bends where a left root and right root of the arch join to the left wing and right wing of the body. These bends cause a slight bending away from horizontal for the arch, to further allow clearance for the spinous process or other anatomical structures to be accommodated. This bend angle is preferably about 15°, but can be bent to a different customizable angle, such as through utilization of a bending tool. Typically this crosslink is formed of a metallic biocompatible material, such as surgical stainless steel or nickel titanium, or other compatible alloys. Through customizing of the body at the bends, by utilization of an appropriate bending tool, such bending can be accommodated, such as to reduce this and angle from 15° down to 0° (or past 0° if desired) and up to a higher angle, such as 45° (or higher).

In addition to the various features disclosed above in the preferred embodiment of this invention, flexibility can also be provided for a surgeon using this invention by providing the crosslinks as a set with different crosslinks therein having different sizes. In such a manner, different vertebrae in the spine can be accommodated, or patients which are larger or smaller can be accommodated. A method of use can include first sizing a crosslink either by selecting from a preset group of crosslinks having a desired size and/or adjusting a length of the crosslink to desired length. Once the crosslink has been appropriately sized it can also be appropriately shaped, such as by changing the bend angle of the arch at the bends or rotating at the joints to cause the extensions to be angled relative to the wings of the body. Finally, the crosslink is put in place and the bolts in the joints are tightened and the studs are tightened so the crosslink is converted into a rigid structure which is clamped to each of the spine rods at ends thereof.

OBJECTS OF THE INVENTION

Accordingly, a primary object of the present invention is to provide a crosslink for fixing a pair of spine rods to each other.

Another object of the present invention is to provide a crosslink which avoids interference with a spinous process or other anatomical structures adjacent to a spine of a patient and particularly at a posterior side of the spine of the patient.

Another object of the present invention is to provide a crosslink which is adjustable in length between ends thereof.

Another object of the present invention is to provide an implantable spine rod crosslink which is changeable in shape to rotate ends thereof relative to each other.

Another object of the present invention is to provide a crosslink which includes an arch at a central portion with a gap therein sized to accommodate a spinous process of a vertebrae therein.

Another object at the present invention is to provide a crosslink which can be modified in shape by bending, especially in an arch area so that an arch of the crosslink can avoid interference with a spinous process of a patient.

Another object of the present invention is to provide a method for securing two spine rods together using a crosslink, and without requiring removal of the spinous process, and allow the crosslink to be placed at an optimal location on the spine rods.

Other further objects of the present invention will become apparent from a careful reading of the included drawing figures, the claims and detailed description of the invention.

BRIEF DESCRIPTION OF THE DRAWINGS

FIG. 1 is a top plan view of a spine rod according to a preferred embodiment of this invention and shown in a maximum length orientation and without any angularity between lateral extensions that join to a central body thereof.

FIG. 2 is a top plan view similar to that which is shown in FIG. 1, but with the crosslink collapsed down to a shortest length configuration.

FIG. 3 is a side elevation view of that which is shown in FIGS. 1 and 2, and with a portion of a spinous process shown in broken lines and illustrating how the arch of the body of the crosslink avoids interference with the spinous process when implanted and holding spine rods together.

FIG. 4 is a front elevation view of that which is shown in FIG. 2, and with a spine rod show in broken lines at one end thereof, illustrating how the crosslink attaches to the spine rod.

FIG. 5 is a partially exploded front elevation view of that which is shown in FIG. 1 and with bolts of joints between the body and extensions of the crosslink exploded away from the joints and with the studs of the clamps exploded away from the extensions.

FIG. 6 is a perspective view of that which is shown in FIG. 5, with the bolts and studs assembled and secured in place.

FIG. 11 is a top plan view of the crosslink of FIGS. 1-8 shown attached to spine rods which are secured to a spine of a patient, and illustrating how the arch of the crosslink curves around the spinous process of adjacent vertebrae and also how the joints can be utilized to adjust length of the crosslink and also to accommodate pivoting, such as to allow for secure attachment to spine rods which are not strictly parallel with each other.

DESCRIPTION OF THE PREFERRED EMBODIMENT

Figure 7:
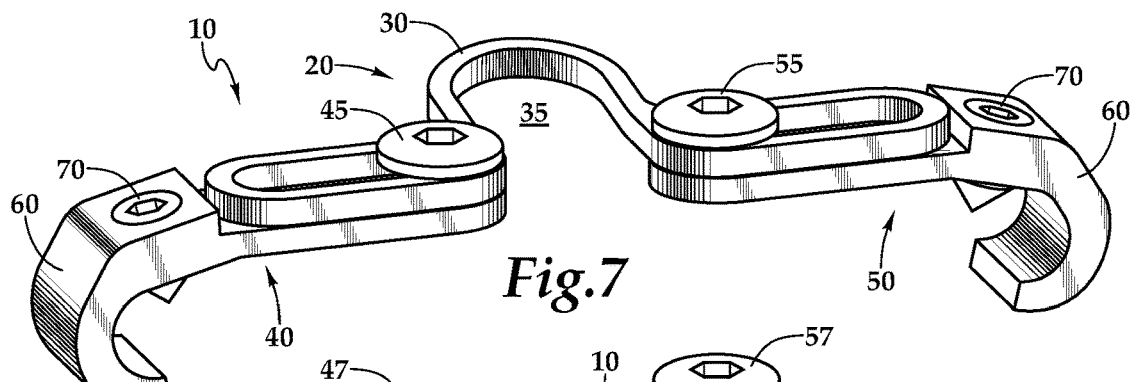
FIG. 7 is a perspective view of that which is shown in FIG. 6, but with the crosslink collapsed into a smallest width configuration.
Figure 8:
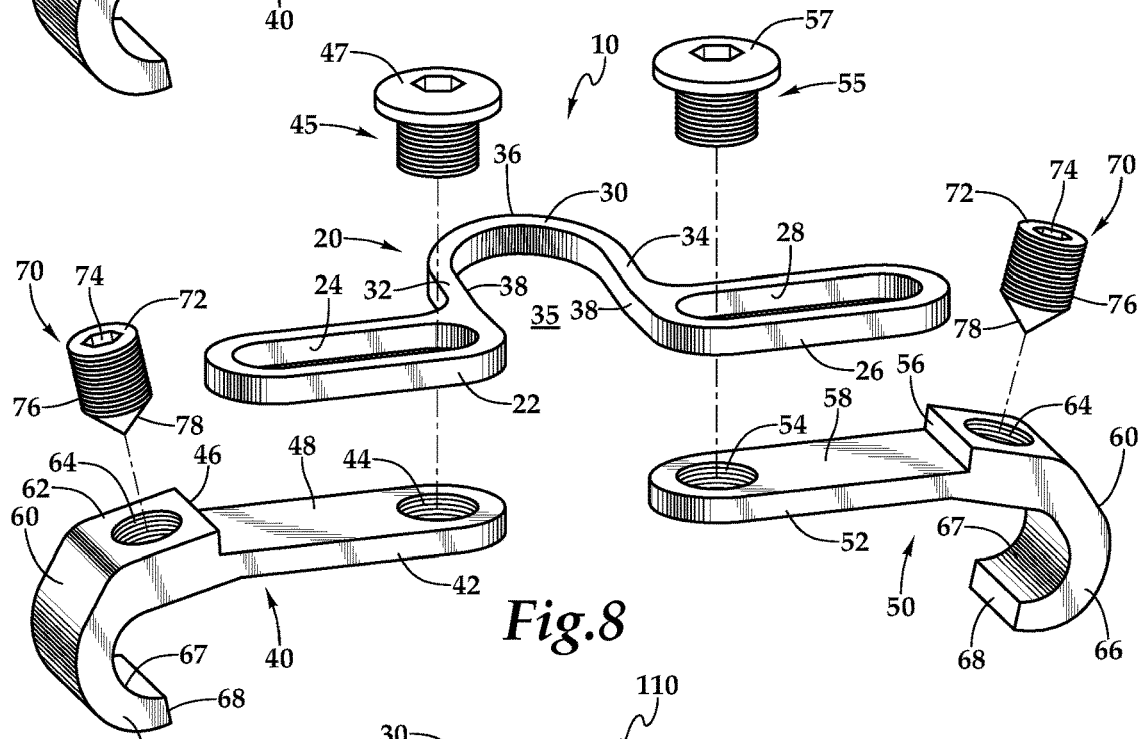
FIG. 8 is a perspective exploded parts view of that which is shown in FIG. 7, and showing a body of the crosslink exploded away from left and right extensions of the crosslink, and showing threaded holes within the extensions for receipt of the bolts and the studs.

Referring to the drawings, wherein like reference numerals represent like parts throughout the various drawing figures, reference numeral 10 is directed to an implantable spine rod crosslink which can be secured to spine rods R such as those fastened to pedicles P of adjacent vertebrae V within a spine S of a patient. The crosslink 10 has a central body 20 featuring an arch 30 therein with a gap 35 which is sized large enough to allow the spinous process SP of a patient to pass through the gap 35 and avoid interference with the crosslink 10.

In essence, and with particular reference to FIGS. 1-4 and 11, basic details of this invention are described, according to a preferred embodiment. The crosslink could be provided as a single monolithic structure with the body 20 supporting spine rod R fasteners at distal ends thereof. Most preferably at least one extension, and in this preferred embodiment a left extension 40 and right extension 50, support clamps 60 (as preferred spine rod R fasteners) at distal ends thereof and with extensions 40, 50 moveably attached to the body 20. The body 20 includes an arch 30 at central portions of the body 20 between left extension 40 and right extension 50. The arch 30 extends around a gap 35 sized to allow the spinous process SP to fit therein. Studs 70 act within the clamps 60 to hold one of the spine rods R within each clamp 60, when the stud 70 is tightened. The preferred spine rod accommodates both length extension and contraction, as well as pivoting at joints between the extensions 40, 50 and the body 20. Also, crosslinks 10 can be provided in various different sizes, such as including the small crosslink 110 (FIGS. 9 and 10) so the different sides of vertebrae can be accommodated. The arch 30 is preferably angled (FIG. 3) with the bend angle δ being preferably adjustable, such as by use of a bending tool.

More specifically, and with particular reference to FIGS. 3 and 5-8, details of the body 20 are described, according to this preferred embodiment. In this embodiment, the body 20 provides a middle portion of the crosslink 10 between the left extension 40 and right extension 50. In alternative embodiments, the body could be formed rigidly with one of the extensions 40, 50, or both of the extensions 40, 50 could be formed along with the body as a single rigid mass, or variations on these extensions 40, 50 could be provided in various other forms of the crosslink according to this invention. The preferred body 20 is a rigid monolithic structure which includes a left wing 22 extending in the left direction and a right wing 26 extending in the right direction, with the left wing 22 and right wing 26 generally extending along a common line. In preferred embodiments, a slot 24 is formed in the left wing 22 and a slot 28 is formed in the right wing 26. These slots 24, 28 accommodate length expansion of the crosslink 10. In alternative embodiments, the slots 24, 28 could be placed within the extensions 40, 50 and threaded holes could be provided in the wings 22, 26 for a general reversal of the joint provided between the slots 24, 28 and the bores 44, 54 and for use by the bolts 45, 55.

The wings 22, 26 transition into an arch 30 portion of the body 20 at bends 38 located at the left root 32 and a right root 34 of this arch 30. The arch 30 extends away from the left root 32 and right root 34 to come together at an apex 36. Preferably the arch 30 starts at the left root 32 and right root 34 with structure extending generally parallel on opposite sides of the gap 35 inboard of the arch 30. After extending linearly some distance, such as a distance similar to a lateral dimension of the wings 22, 26, the apex 36 of the arch 30 is provided by having these two portions of the body 20 curve toward each other and join together the apex 36. This curving structure is shown in this embodiment with a square cross-section. This cross-section could be rectangular or oval or circular or other shape in cross-section. Most preferably, the arch 30 and other portions of the body 20 are sufficiently thick and formed from sufficiently strong and rigid materials that flexing of the crosslink 10 is generally eliminated, or reduced to a level similar (at least within about an order of magnitude) to an amount of flex contained within the spine rods R, generally.

The bends 38 cause the arch 30 to be elevated above other portions of the body 20 at least slightly. As depicted in FIG. 3, these bends are shown causing the arch 30 to angle at an angle δ away from a horizontal extension plane, so that the apex 36 of the arch 30 is elevated above other portions of the crosslink 10. This angle δ is shown at approximately 15°. However, the angle could be as little as 0° (or less) or as great as 45° or more. As these angles are measured away from horizontal, the angle of δ depicted would be 165°. If the arch 30 were flat, the angle δ depicted would be 180°. This angle can be adjusted, such as by utilizing an appropriate bending tool (pliers, a holding and bending jig or vice, etc.), and by forming the body 20 from a suitable material which facilitates such a bending. Materials from which the body 20 (and other portions of the crosslink 10) would typically be formed include surgical stainless steel or various alloys of titanium which have sufficient bio-compatibility properties. The body 20 is sized so that such bending is facilitated, but after being bent, the crosslink 10 still maintains this angle and desired rigidity.

With continuing reference to FIGS. 5-8, particular details of the left extension 40 and right extension 50 are described, according to this preferred embodiment. In alternative embodiments, one or both of the extensions 40, 50 could be affixed permanently to the body 20. However, in this preferred embodiment the left extension 40 and the right extension 50 are movably attached to the body 20, through joints provided between the slots 24, 28 and the wings 22, 26 of the body 20 and through the bores 44, 54 and bolts 45, 55 associated with extensions 40, 50.

Each extension 40, 50 is generally an elongate rigid structure with a proximal end defined by a base 42, 52. Each base 42, 52 has a bore 44, 54 therein. These bores 44, 54 are threaded so that a bolt 45, 55 can pass through one of the slots 24, 28 and then into one of the bores 44, 54 for tightening of this joint between the body 20 and extensions 40, 50.

In particular, each bolt 45, 55 has a head 47, 57 and a threaded shaft. As the bolts 45, 55 are rotated in a tightening direction, the heads 47, 57 are caused to pinch against the wings 22, 26 of the body 20 and cause the body 20 to be securely attached to the base 42, 52 of the extension 40, 50. If desired, this clamping effect could be increased by knurling or otherwise roughening surfaces of the wings 22, 26 which abut against the base 42, 52. Other fasteners could replace the bolts 45, 55, such as rivets or bolt and nut pairs, etc.

The base 42, 52 preferably has an upper surface in the form of a flat 48, 58 which extends away from the proximal end of each extension 40, 50 until it reaches a step 46, 56 and transitions the extensions 40, 50 into a thicker cross-sectional form as they transition into the clamps 60. The flat 48, 58 provides a surface against which one of the wings 22, 26 of the body 20 can rest to help in supporting the overall crosslink 10 in various different lengths and joint orientations.

Distal ends of each extension 40, 50 include a clamp 60 (as a preferred form of spine rod R fastener) thereon which are preferably mirror images of each other and so are provided with similar reference numerals. Each clamp 60 includes an upper facet 62 which is preferably angled slightly relative to the adjacent flat 48, 58 of the adjacent extension 40, 50. A hole 64 passes through the upper facet 62 down to a lower surface of the clamp 60. This hole 64 is threaded with female threads to engage with a stud 70.

Beyond the upper facet 62, the clamp 60 transitions into a curve 66 which it curves first downwardly and then inwardly back generally toward a center of the crosslink 10 where the body 20 is located. This curve 66 continues until it reaches a tip 68 which is beneath the upper facet 62. The inner surface 67 of the curve 66 is preferably smooth and cylindrical in form, having a diameter similar to that of a spine rod R (FIG. 4) to allow the clamp 60 of the crosslink 10 to attach securely to the spine rod R.

The stud 70 that is placed within the hole 64 in the clamp 60 includes a top 72 with a torque tool receiving recess 74 therein. The stud 70 includes a threaded shaft 76 extending down from the top 72 to a conical tip 78 (or tip having some other form). The stud 70 is tightened by rotation within the threaded hole 64 of the clamp 60, the conical tip 78 is caused to move down towards the tip 68 of the clamp 60 and can thus secure a spine rod R therein. By providing a conical tip 78, tightening of the stud 70 tends to push the spine rod R against the inner surface 67 for secure holding within the clamp 60. Motion of the stud 70 is depicted as being along arrow C of FIG. 4.

Figure 9:
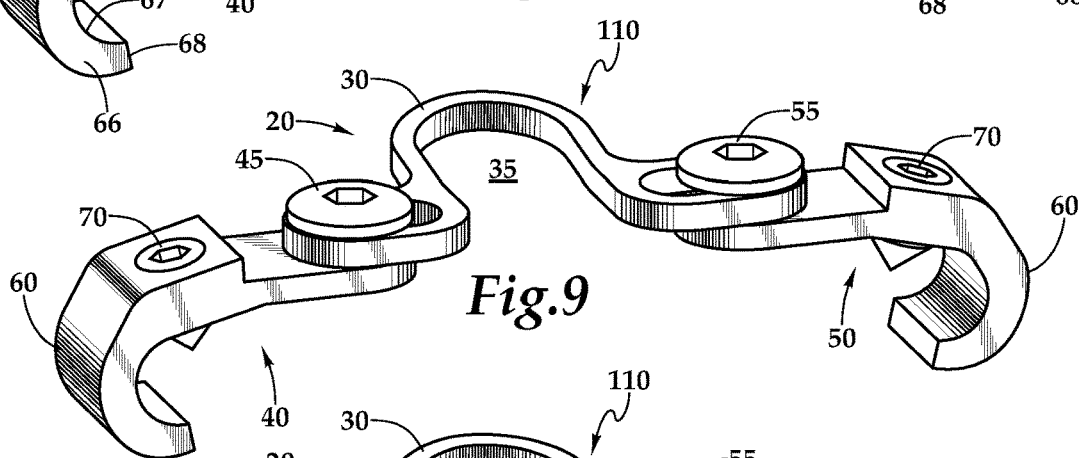
FIG. 9 is a perspective view of an alternative embodiment small crosslink which is similar in form to the crosslink of FIGS. 1-8, except that it is shorter in width and has a lesser amount of adjustability in length.
Figure 10:
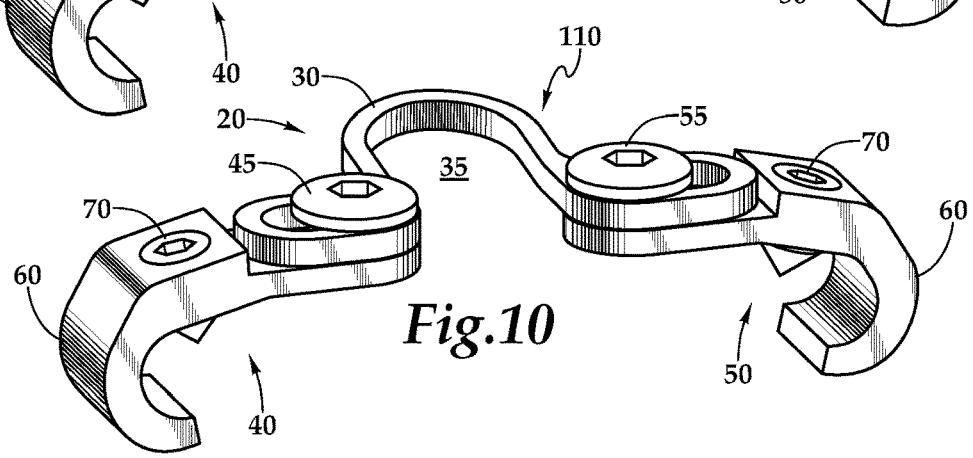
FIG. 10 is a perspective view of that which is shown in FIG. 9, but in a shortest length configuration.

FIGS. 9 and 10 show an alternative small crosslink 110 which is preferably similar in all respects to the crosslink 10 of the preferred embodiment except that the wings of the body 20 are shorter and the corresponding slots therein are shorter. Similarly, the extensions 40, 50 thereof are shorter in length. Such a small crosslink 110 is beneficial for smaller vertebrae and/or smaller patients.

A kit of crosslinks having multiple different sizes can be provided, with the adjustability of each crosslink further facilitating optimal length sizing of the crosslink 10 when joining spine rods R together. Such length adjustability is depicted by arrows A and B for the left extension 40 and right extension 50, respectively (FIGS. 1 and 2). Similarly, these joints also facilitate some degree of pivoting of the extensions 30 relative to the body 20 (FIG. 11). In particular, while the extensions 40, 50 can extend along a line parallel with the wings 22, 26 of the body 20 and co-linear with each other, the joints located at the bolts 45, 55 can accommodate different angles. For instance, if a straight orientation represents an angle α of 180° and angle β of 180° (FIG. 11) at these two joints, FIG. 11 depicts angles of about 175° for angle α and 175° for angle β. These angles could be adjusted to be greater or lesser than that amount and up to perhaps as great as 225° or as little as 135°, so that different spine rod R orientations can be accommodated, and to otherwise allow for the arch 30 of the body 20 to be position where desired to avoid interference with the spinous process SP or other anatomical features of a patient.

In use and operation according to this preferred embodiment, and with continuing reference primarily to FIGS. 1-4 and 11, the crosslink 10 would typically be utilized as follows. First, a surgeon or other medical practitioner will identify the spine rods R are to be joined together. A general distance between spine rods R and orientation of the spine rods R is studied. A crosslink 10, 110 is then selected from a group of spine rods R which is generally of an appropriate length. The spine rod R would typically be initially provided in a sterilized form and with the bolts 45, 55 loose but still holding the extensions 40, 50 to the body 20. Also, the studs 70 would be generally in a retracted position but already threaded somewhat into the clamps 60.

The surgeon then manipulates the joints at the bolts 45, 55 to cause the crosslink 10, 110 to have a desired length and angular shape at the joints. The surgeon simultaneously places the crosslink 10, 110 down causing the spine rods R to fit within the clamps 60 and with the spinous process SP of an adjacent vertebrae V passing through the gap 35 in the arch 30 of the body 20.

The surgeon can study the position of the crosslink 10, 110 and verify that it is positioned as desired. If needed, the arch 30 can be bent at the bends 38, utilizing a bending tool, such as pliers, to provide still greater clearance for the spinous process SP or other adjacent anatomical structures. Finally, the bolts 45, 55 are tightened utilizing a torque applying tool until these joints are fixed. The studs 70 are tightened (either before or after bolt 45, 55 tightening), preferably utilizing the same torque applying tool, until the studs 70 have tightly secured the clamps 60 to the spine rods R. If multiple crosslinks are to be installed, the surgeon continues with the next crosslink 10, 110 until all crosslinks 10, 110 have been placed. Should removal be required, a reverse process can be followed where the studs 70 are rotated to loosen them off of the spine rods R, (and optionally the bolts 45, 55 also) and then the crosslink 10, 110 can be lifted and removed. If needed, the joints at the bolts 45, 55 (or at least one of them) can be loosened to allow the clamps 60 to release off of the spine rods 60 sufficiently to allow removal.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A crosslink for attaching together spine rods for fastening to a spine of a patient, the crosslink comprising in combination:
   a body including an arch between a left wing and a right wing, said left wing and said right wing extending away from each other;
   said arch extending in a lateral direction which is lateral to a direction in which said left wing and said right wing extend away from each other;
   a gap within said arch defining a space between said left wing and said right wing;
   a pair of spine rod fasteners;
   wherein said left wing and said right wing are each coupled to an extension structure separate from said body and movable relative to said body, each said extension including one of said spine rod fasteners thereon;
   wherein said extensions are extendable away from and toward said body through joints between said extensions and said body; and
   wherein said arch angles upwards from roots of said arch which are closer to said left wing or said right wing than to an apex of said arch midway between said roots, said upwards direction perpendicular to said lateral direction that said arch extends away from a line between said left wing and said right wing, and also perpendicular to said line between said left wing and said right wing.

2. The crosslink of claim 1 wherein said extensions are also pivotable relative to said body through said joints between said extension and said body.

3. The crosslink of claim 2 wherein a left extension is coupled to said left wing through a joint therebetween and a right extension is coupled to said right wing through a joint therebetween, each of said joints including a slot and a hole aligned together, and with threads in said hole and with a threaded fastener passing through said slot and into said threaded hole to adjustably fasten said left wing to said left extension and said right wing to said right extension, each at an adjustable angle and an adjustable extension distance away from said gap.

4. The crosslink of claim 3 wherein said spine rod fasteners each include a clamp at a tip of each of said left extension and said right extension, each clamp including a curve having a curving inner surface, and with a stud threadably attached adjacent to said curve with tightening of said stud by threading translation, causing a space between said curving inner surface of said clamp and a tip of said stud to be reduced for capturing the spine rod therebetween.

5. The crosslink of claim 1 wherein said arch is formed of a material which is bendable such that an angle of upward extension of said arch can be modified.

6. The crosslink of claim 1 wherein said spine rod fasteners are configured to capture the spine rod extending in a spine rod direction, said lateral direction of extension of said arch being parallel with said spine rod direction and perpendicular to said upwards direction by which said arch angles upwards from said roots of said arch to said apex of said arch midway between said roots.

7. The crosslink of claim 6 wherein said lateral direction of extension of said arch is greater than a width that said wings exhibit along said spine rod direction.

8. An implantable spine rod crosslink, comprising in combination:
- a body including an arch between a left extension and a right extension said left extension coupled to said body through a left joint therebetween, and said right extension coupled to said body through a right joint therebetween;
- said arch extending lateral to a direction in which said left extension and said right extension extend away from said body;
- a gap within said arch, defining a space between said left extension and said right extension;
- spine rod fasteners on each of said left extension and said right extension;
- wherein at least one of said extensions is extendable away from said body through at least one of said joints between said extensions and said body; and
- wherein said arch angles upwards from roots of said arch which are closer to a left wing or a right wing than to an apex of said arch midway between said roots, said upwards direction perpendicular to said lateral direction that said arch extends away from a line between said left wing and said right wing, and also perpendicular to said line between said left wing and said right wing.

9. The spine rod crosslink of claim 8 wherein said arch is formed of a material which is bendable such that an angle of upward extension of said arch can be modified.

10. The spine rod crosslink of claim 8 wherein at least one of said extensions is also pivotable relative to said body through at least one of said joints between said extensions and said body.

11. The spine rod crosslink of claim 10 wherein said body has said left wing and said right wing extending away from each other and away from said gap, and wherein said left extension is coupled to said left wing through said left joint therebetween and said right extension is coupled to said right wing through said right joint therebetween, each of said joints including a slot and a hole aligned together and with threads in said hole and with a threaded fastener passing through said slot and into said threaded hole to adjustably fasten said left wing to said left extension and said right wing to said right extension, each at an adjustable angle and an adjustable extension distance away from said gap.

12. The spine rod crosslink of claim 11 wherein said spine rod fasteners each include a clamp at a tip of each of said left extension and said right extension, each clamp including a curve having a curving inner surface, and with a stud threadably attached adjacent to said curve with tightening of said stud by threading translation, causing a space between said curving inner surface of said clamp and a tip of said stud to be reduced for capturing the spine rod therebetween.

13. The spine rod crosslink of claim 8 wherein said spine rod fasteners are configured to capture the spine rod extending in a spine rod direction, said lateral direction of extension of said arch being parallel with said spine rod direction and perpendicular to said upwards direction by which said arch angles upwards from said roots of said arch to said apex of said arch midway between said roots.

14. The spine rod crosslink of claim 13 wherein said lateral direction of extension of said arch is greater than a width that said wings exhibit along said spine rod direction.

15. An implantable spine rod crosslink, comprising in combination:
- a body including an arch between a left extension and a right extension said left extension coupled to said body through a left joint therebetween, and said right extension coupled to said body through a right joint therebetween;
- said arch extending lateral to a direction in which said left extension and said right extension extend away from said body;
- a gap within said arch, defining a space between said left extension and said right extension;
- spine rod fasteners on each of said left extension and said right extension;
- wherein at least one of said extensions is extendable away from said body through at least one of said joints between said extensions and said body; and
- wherein said spine rod fasteners are configured to capture separate ones of a pair of spine rods extending in a spine rod direction, said lateral direction of extension of said arch being parallel with said spine rod direction and perpendicular to said upwards direction by which said arch angles upwards from said roots of said arch to said apex of said arch midway between said roots.

16. The spine rod crosslink of claim 15 wherein said lateral direction of extension of said arch is greater than a width that left and right wings of said body exhibit along said spine rod direction.

* * * * *